United States Patent
Synowicki et al.

(10) Patent No.: US 7,239,391 B2
(45) Date of Patent: Jul. 3, 2007

(54) METHOD OF ANALYSIS OF MULTIPLE LAYER SAMPLES

(75) Inventors: Ronald A. Synowicki, Lincoln, NE (US); Craig M. Herzinger, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 230 days.

(21) Appl. No.: 11/098,669

(22) Filed: Apr. 2, 2005

(65) Prior Publication Data

US 2005/0179897 A1 Aug. 18, 2005

Related U.S. Application Data

(63) Continuation-in-part of application No. 10/238,241, filed on Sep. 10, 2002, now Pat. No. 6,937,341, and a continuation-in-part of application No. 10/194,881, filed on Jul. 15, 2002, now Pat. No. 6,940,595, and a continuation-in-part of application No. 09/916,836, filed on Jul. 27, 2001, now Pat. No. 6,636,309, and a continuation-in-part of application No. 09/756,515, filed on Jan. 9, 2001, now Pat. No. 6,455,853.

(60) Provisional application No. 60/559,559, filed on Apr. 3, 2004, provisional application No. 60/305,535, filed on Jul. 14, 2001.

(51) Int. Cl.
  *G01N 21/41* (2006.01)
  *G01J 4/00* (2006.01)
  *G01B 11/28* (2006.01)

(52) U.S. Cl. ............... 356/369; 356/128; 356/630

(58) Field of Classification Search ............... 356/128, 356/364, 369, 630; 250/559.09, 559.11, 250/559.27
See application file for complete search history.

(56) References Cited

U.S. PATENT DOCUMENTS

| | | | |
|---|---|---|---|
| 4,472,633 A | 9/1984 | Motooka | 250/338 |
| 4,807,994 A | 2/1989 | Felch et al. | 356/326 |
| 5,486,701 A | 1/1996 | Norton et al. | 250/372 |
| 5,625,455 A | 4/1997 | Nash et al. | 356/369 |
| 5,936,734 A * | 8/1999 | Johs et al. | 356/364 |
| 6,049,220 A | 4/2000 | Borden et al. | 324/765 |
| 6,455,853 B2 | 9/2002 | Herzinger et al. | 250/341.1 |
| 6,636,309 B1 | 10/2003 | Johs et al. | 356/369 |
| 6,798,511 B1 * | 9/2004 | Zhan et al. | 356/369 |
| 7,110,912 B1 * | 9/2006 | Tiwald | 702/170 |

OTHER PUBLICATIONS

"P-N Junction-Based Wafer Flow Process For Stencil Mask Fabrication", Rangelow et al., J. Vac. Sci. Technology B, Nov./Dec. p. 3592 (1998); and.

"Application of IR Variable Angle Spectroscopic Ellipsometry To The Determination Of Free Carrier Concentration Depth Profiles", Tiwald et al., Thin Film Solids 313-314, p. 661, (1998).

"Optical Analysis of Complex Multilayer Structures Using Multiple Data Types", Johns et al., SPIE vol. 2253, (1994).

J.A. Woollam Co. Inc. 2002 flyer is identified, as it included an article on global fitting to provide starting values for entry to a regression procedure.

* cited by examiner

*Primary Examiner*—Roy M. Punnoose
(74) *Attorney, Agent, or Firm*—James D. Welch (57) ABSTRACT

Spectroscopic ellipsometer system(s) mediated methodology for quantifying layer defining parameters in mathematical models of samples which contain a plurality of layers of different materials, at least some of which are absorbing of electromagentic radiation, wherein an acquired data set is not sufficient to allow definite one for one parameter evaluation, and wherein a global fit procedure can be applied to obtain good parameter starting values for use in a parameter evaluating regression procedure.

28 Claims, 3 Drawing Sheets

METHOD OF ANALYSIS OF MULTIPLE LAYER SAMPLES

This Application is a CIP of application Ser. No. 10/238,241 Filed Sep. 10, 2002, now U.S. Pat. No. 6,937,341, and a CIP of Ser. No. 09/756,515 Filed Jan. 9, 2001, (now U.S. Pat. No. 6,455,853); and Claims benefit of provisional Application Ser. No. 60/559,559 Filed Apr. 3, 2004. This Application is also a CIP of Ser. No. 10/194,881 Filed Jul. 15, 2002 now U.S. Pat. No. 6,940,595 and a CIP of Ser. No. 09/916,836 Filed Jul. 27, 2001, (now U.S. Pat. No. 6,636,309), and therevia Claims Benefit of Provisional 60/305,535 Filed Jul. 14, 2001.

TECHNICAL FIELD

The present invention relates to non-destructive characterization of sample systems comprised of a plurality of layers of different materials, and more particularly to spectroscopic ellipsometer system(s) mediated methodology for quantifying layer defining parameters in mathematical models of samples comprised of two substantially parallel sides which are separated by a thickness which contains a plurality of layers of different materials.

BACKGROUND

Obtaining data to enable Ellipsometric analysis of all layers of a sample which comprises a plurality of layers of different materials can be difficult. This is because electromagnetic radiation caused to impinge upon a surface thereof at an oblique angle is generally most sensitive to the outermost layers, particularly if one or more layers is absorbing. For instance, in the case of Three Layers "A", "B" and "C", electromagnetic radiation directed at an oblique angle to the surface of the "A" material is not always sensitive to the "C" material, when layers above are substantially opaque so that layers therebelow cannot be investigated therethrough. A solution is to acquire data from the front and back of the sample and use both data sets in analysis, possibly in combination with acquisition of transmission data through the sample using a beam directed substantially along a normal to the top surface, or at an angle with respect thereto. (Note, not all layers need be absorbing for the present invention to be of value).

A Patent to Herzinger et al. U.S. Pat. No. 6,455,853 Issued Sep. 24, 2002, from which this Application is a CIP via application Ser. No. 10/238,241, describes use of data obtained from two sides of a sample. Said 853 Patent taught utilizing Spectroscopic IR and NIR data sets obtained from the front and back of a sample, to evaluate Thickness and Impurity Profile defining parameters therein, as opposed to a sample comprised of a plurality of layers of different materials.

Further disclosed is a U.S. Pat. No. 6,636,309 to Johs et al., from which this Application is a CIP via application Ser. No. 10/194,881. Said Patent describes fabrication of narrow bandpass and band reject stacked filters using beams of electromagnetic radiation which are directed at an oblique angle of incidence to a surface thereof to monitor real time deposition. Said Patent identifies use of an intermediate wavelength band which surrounds, for instance, a narrow passband, in which narrow range reflectivity is nearly constant. It is noted that the materials of the multiple layers in the stacked filter are substantially transparent under the teachings of the 309 Patent, and that the present invention is appropriate for use with multiple layers of materials which are to various degrees, absorbing.

In addition, U.S. Pat. No. 4,472,633 to Motooka is disclosed as it describes use of linearly polarized infrared light to investigate semiconductor wafers. Plots of Ellipsometric PSI vs. Ellipsometric DELTA, as a function of Angle of Incidence and/or Wavelength, for various carrier density profiles and depths are determined. Ellipsometric data obtained from a sample wafer is then utilized to plot Ellipsometric PSI vs. Ellipsometric DELTA, as a function of Angle of Incidence and/or Wavelength, and the results compared to the known plots. Close correlation between sample wafer and a known Ellipsometric PSI vs. Ellipsometric DELTA, as a function of Angle of Incidence and/or Wavelength, is indicative of the sample having a doping profile and depth similar to that of the wafer from which the known Ellipsometric PSI vs. Ellipsometric DELTA data was obtained. Data is described as obtained utilizing monochromatic light, even though different wavelengths are used in succession where wavelength is the independent variable.

Another Patent, U.S. Pat. No. 4,807,994 to Felch et al., describes a non-ellipsometric method of mapping ion implant dose uniformity. Monochromatic Electromagnetic radiation with a bandwidth of not more than 1 nm, (chosen for sensitivity to sample parameters being measured), which has interacted with a sample in Reflectance or Transmission, is monitored by a Spectrophotometer and the results compared to previously obtained similar data regarding film thickness and ion implant doses, and similarities determined.

U.S. Pat. No. 5,486,701 to Norton et al., describes a non-ellipsometric approach simultaneously utilizing wavelengths in both UV and Visible wavelength ranges to enable calculating a ratio thereof, which in turn is utilized to determine thin film thicknesses.

U.S. Pat. No. 6,049,220 to Borden et al., describes apparatus and method for evaluating semiconductor material. In a major implementation thereof, two beams are caused to illuminate a sample, one having energy above the bandgap and the other having energy near or below the bandgap. The second beam, after interaction with the sample, is monitored and change therein caused by said interaction is indicative of carrier concentration. It is noted that reflectance of an electromagnetic beam from a sample is a function of carrier concentration.

U.S. Pat. No. 5,625,455 to Nash et al. and U.S. Pat. No. 5,900,633 to Solomon et al. were provided by the Examiner in Examination of Parent application Ser. No. 09/756,515, (now U.S. Pat. No. 6,455,853).

A Patent to Herzinger et al., U.S. Pat. No. 5,796,983 is identified, and incorporated by reference herein, as it describes Parameter Models which can be applied in practice of the present invention.

Known relevant art includes Articles:

"P-N Junction-Based Wafer Flow Process For Stencil Mask Fabrication", Rangelow et al., J. Vac. Sci. Technology B, Nov/Dec P. 3592 (1998); and "Application of IR Variable Angle Spectroscopic Ellipsometry To The Determination Of Free Carrier Concentration Depth Profiles", Tiwald et al., Thin Film Solids 313-314, P661, (1998).

"Optical Analysis of Complex Multilayer Structures Using Multiple Data Types", Johs et al., SPIE Vol. 2253, (1994). This paper describes use of ellipsometric data obtained from both sides of a fused silica substrate which has a layer of chromium on one surface thereof, in combination with transmission intensity data, to determine optical constants and thicknesses. This paper, however, does not address the case in which a plurality of layers of material are present on at least one surface of a sample, and it is desired to determine optical constants and thicknesses for each, and a data set consisting of two PSI and two DELTA values, (obtained by ellipsometric investigation from both sides of a sample), plus a transmission data set, is insufficient to directly evaluate optical constants and thicknesses for each layer present at each wavelength. The 853 Patent identified above, and from which this Application is a CIP via Pending application Ser. No. 10/194,881, provides the necessary seed of additional insight which has led to the present invention.

In addition, a J. A. Woollam Co. Inc. 2002 flyer is identified, as it included an article on global fitting to provide starting values for entry to a regression procedure.

A need remains for a method of utilizing data sets to practically determine optical constants and thicknesses for each layer in a multiple layer sample, which data set, on a wavelength by wavelength basis, is insufficient to provide accurate determination of all optical constants and thicknesses for each of a plurality of layers on a substrate.

DISCLOSURE OF THE INVENTION

The present invention is a modified embodiment of the teachings in a Patent to Herzinger et al. U.S. Pat. No. 6,455,853, from which this Application is a CIP. Where the 853 Patent teaches investigation of a single substrate which contains a profile of impurities near one surface thereof, the presently disclosed invention teaches a similar method to investigate a sample comprised of a substrate and a plurality of surface layers. The approach disclosed in said 853 Patent enables use of ellipsometric data obtained from both sides of a sample substrate to evaluate parameters in a mathematical model which characterizes the impurity profile, using a parameterized mathematical model. The present invention expands on this theme, and in particular utilizes parameterization of optical constants, in each of a pluraity of layers of different materials, (or at least a majority of layers where more than two are present on a substrate), as an approach to enabling determination of real and imaginary parts of optical constants and thicknesses for at least two layers, (ie. Six (6) unknowns for a multiplicity of wavelengths), using a data set of Five (5) or Six (6) or Seven (7) Knowns, (ie. Two (2) PSI and Two (2) DELTA obtained by Relection Ellipsometry taken from both sides of a Substrate, and Transmission Data, (which provides One (1) data set for Intensity measurements, and/or Two (2) data sets for Ellipsometric measurements). The present invention is found in the use of Five (5) Data sets. In some cases, the present invention's use of Parameterization of Optical Constants over a range of wavelengths for a plurality of Layers in a sample, even enables accurate determination of additional parmeters which characterize the sample, such as interface mixing, surface roughness, thickness nonuniformity, grading within layers, and birefringence along with the optical constant and thicknesses for each layer of material, using the data set of Five (5) or Six (6) or Seven (7) knowns. In every case, however, the present invention is found in evaluating more parameters than there are data to enable direct one for one determination.

A general present invention method of evaluating a sample comprised of at least:
  material 1 and material 2;

present on at least one surface of a substrate having first and second substantially parallel sides, then comprises the steps of:

a) using published data and/or separate samples of material from each layer and/or educated guessing to determine starting values for n and k for said materials 1 and 2 seperately over a range of wavelengths, and therefrom determining initial values for parameters in a parameterized mathematical model therefore;

practicing steps b and c in either order or simultaneously:
b) obtaining reflective spectroscopic ellipsometric data from both first and second sides of said sample, and transmission data from at least one side thereof to provide two PSI, two DELTA and one transmission data sets;
c) providing a mathematical model of said sample comprising n and k and thickness for each of the material layers, said n and k being parameterized over a plurality of wavelengths, said n and k for each material being parameterized over a plurality of wavelengths as determined in step a;
d) regressing said mathematical model identified in step c, simultaneously onto the five data sets identified in step b;

to evaluate said n, k and thickness defining parameters for the material 1 and material 2 layers in the wavelength range over which said n and k values are parameterized.

The mathematical model can further comprise at least one parameter which characterizes at least one selection from the group consisting of:
  interface mixing;
  surface roughness;
  thickness nonuniformity;
  grading within layers;
  birefringence; and
  incoherent back-surface reflections.

In general, an additional step involves determining at least one wavelength range in which said ellipsometric data is sensitive to a desired parameter, and using only ellipsometric data at said wavelengths in the regression procedure, with ellipsometric data at wavelengths not sensitive to said grading not being used in said regression procedure. The wavelength range and/or step size selected in ellipsometric data obtained from the first side of said sample can be different than the wavelength range selected in ellipsometric data obtained from the second side of said sample.

Said present invention method of evaluating a sample can involve a sample comprised of:
  material 1, material 2 and material 3;

present on at least one surface of a substrate having first and second substantially parallel sides;

said method sequentially comprising the steps of:
a) using published data and/or separate samples of material from each layer and/or educated guessing, determining starting values for n and k for said material in each layer separately;

practicing steps b and c in either order:
b) obtaining reflective spectroscopic ellipsometric data from both first and second sides of said sample, and transmission data from least at least one side thereof to provide two PSI, two DELTA and one transmission data sets;
c) providing a mathematical model of said sample comprising n and k and thickness for each of the material 1, material 2, and material 3 layers, said n and k for each material being parameterized over a plurality of wavelengths;
d) regressing said mathematical model which comprises said nine parameters identified in step c, simultaneously onto the five data sets identified in step b;

to evaluate n, k and thickness defining parameters for each said material 1, material 2, and material 3 layers in the wavelength range over which said n and k values are parameterized.

It is to be understood that in the foregoing present invention method, it is possible to fix the optical constants and/or thickness of at least one of the layers and practice the method to the end that parameters for the other layers are evaluated.

The mathematical model can again further comprise at least one parameter which characterizes at least one selection from the group consisting of:
  interface mixing;
  surface roughness;
  thickness nonuniformity;
  grading within layers;
  birefringence; and
  incoherent back-surface reflections.

The mathematical model can again comprise intermixing between at least two layers, and an additional step can involve determining at least one wavelength range in which said ellipsometric data is sensitive thereto, and using only ellipsometric data at said wavelengths in the regression procedure, with ellipsometric data at wavelengths not sensitive to said intermixing not being used in said regression procedure. Intermixing can be present, for instance, between materials in at least one selection from the group consisting of:
  material 1 and material 2;
  material 2 and material 3;
where said materials provide a stacked sequence on one side of a sample substrate.

Another recital of a method of quantifying defining parameters for a plurality of layers of different materials present on a substrate in a sample, comprises obtaining reflection ellipsometric data from both first and second sides of a sample comprising a plurality of layers of different materials and providing a mathematical model of said sample, then regressing said mathematical model onto data obtained from said first and second sides of said sample by a selection from the group consisting of:
  utilizing the data sets obtained from first and second sides of the sample simultaneously;
  utilizing the data sets obtained from said first and second sides of the sample independently; and
  utilizing the data sets obtained from first and second sides of the sample both independently and simultaneously.
to evaluate said sample layer defining parameters.

Said method can further comprise obtaining transmission ellipsometry and/or intensity data from at least one of said first and second sides of said sample, and including it in the regression evaluation of said sample layer defining parameters.

It is specifically noted that the methodology can be applied to samples which have layers on both sides of a substrate, (eg. one of materials 1 and 2 are present on one surface and the other thereof, or materials 1 and 2 can be on the same side and a material 3 be present on the other surface). Further, reflective and transmissive data sets can be obtained for one or more angles-of-incidence. It is again noted that the mathematical model can further comprise parameters which describe grading within layers, intermixing between adjacent layers and/or surface oxide layers and surface roughness, and additional steps can involve selected use of wavelengths and/or step size, (ie. the wavelength range between wavelengths at which data is acquired), used to obtain ellipsometric data from the first side of said sample which are not the same wavelengths used to obtain ellipsometric data from the second side of said sample, and transmission data can be spectroscopic. Further, the presently disclosed methodology can be applied to samples which comprise more than three layers, but it becomes progressively more difficult to evaluate characterizng parameters in all layers as the number of layers is increased, with the acquired data.

It is noted that one approach to obtaining good initial "educated guess" values for characterizing parameters in a mathematical model of a sample comprising a plurality of layers, is a technique termed "Global Fitting". Particulary where a multi-layer sample is first approached, it is necessary to arrive at good starting values for n and k and thickness for each of the layers, such that when used in a regression procedure the regression routine does not provide answers corresponding to a false minimum in an error based quality of parameter, such as a Mean Squared Error (MSE). It is first noted that a Square Error is generally calculated by summing a squared difference between empherical data and mathematical model calculated data over a range of independent variable. The terminology "Mean" refers to Square Error calculations which impose weighting to emphasize more significant values in the calculation. Continuing, the "Global Fit" approach provides that a multiplicity of reasonable combinations of parameters that are to be fit to empirical data by a regresion procedure be tested, and the combination which provides the lowest Square Error value be identifed. That combination of values is then entered to the regression procedure which serves to provide best fit values. The Global Fit procedure helps insure that the regression procedure does not return values that correspond to a false Square Error minimum.

A method of evaluating a sample comprised of at least:
  material 1 and material 2;

present on at least one surface of a substrate having first and second substantially parallel sides;

then can sequentially comprise the steps of:

practicing steps a and b in either order or simultaneously:
  a) obtaining reflective spectroscopic ellipsometric data from both first and second sides of said sample, and transmission data from at least one side thereof to provide two PSI, two DELTA and transmission intensity and/or transmission ellipsometric PSI and DELTA data sets;
  b) providing a mathematical model of said sample comprising n and k and thickness for each of the material layers, said n and k being parameterized over a plurality of wavelengths;
  c) determining starting values for n and k and thickness for said material 1 and material 2 parameters in a parameterized mathematical model, by application of a global fit procedure which comprises scanning parameter values through a grid range thereof to determine a combination of values which provides the lowest square error between empirical data and values calculated by use of the mathematical model;
  d) utilizing starting values determined in step c regressing said mathematical model identified in step c, simulaneously onto the five or six data or seven sets identified in step a;

to evaluate said n, k and thickness defining parameters for the material 1 and material 2 layers in the wavelength range over which said n and k values are parameterized.

It is to be understood that where two material layers are present, material 1 can be present on one side of said substrate and material 2 present on the other side of said sample, or both can be present on the same side, and where three material layers are present, all three can be present on one side of a substrate, or two can be present on one side thereof, with the third present on the other side.

It is specifically noted that the present invention methodology is characterized in that the obtained data is insufficient to directly one for one evaluate all parameters of the mathematical model over the wavelength range.

The disclosed invention will be better understood by reference to the Detailed description Section, in combination with the Drawings.

SUMMARY OF THE INVENTION

It is therefore a purpose and/or objective of the present invention to teach a method of evaluating defining parameters for a plurality of layers of different materials, (at least one of said layers being absorbing), present in layers on a substrate which has substantially parallel sides, wherein reflection ellipsometric data is obtained from both sides thereof, and a mathematical model which contains parameters which describe the layers is then regressed onto data obtained from both said sides of the sample, sequentially and/or simultaneously.

It is another purpose and/or objective of the present invention to teach obtaining transmission ellipsometric and/or intensity data and include it with ellipsometric reflection data obtained from first and second substantially parallel sides of a multi-layer sample in a regression procedure to evaluate parameters in a mathematical model thereof.

It is another purpose and/or objective yet of the present invention to teach application of a global fit procedure to determine good initial values for layer characterizing optical constant and thickness and the like parameters, and entering said good initial values into the a regression procedure.

It is a specific purpose and/or objective of the present invention to teach methodology for evaluation of parameters in a mathematical model of a sample, which is characterized in that obtained data is insufficient to directly one for one evaluate all parameters of the mathematical model over the wavelength range.

Other purposes and/or objectives of the present invention will become apparent upon a reading of the Specification and Claims.

DETAILED DESCRIPTION

Figure 1:
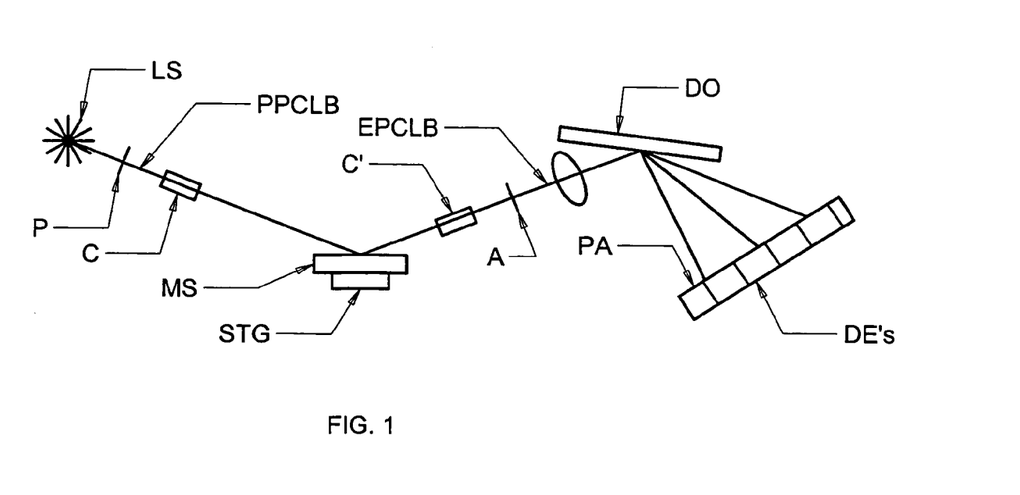
FIG. 1 shows a demonstrative ellipsometer system which simultaneously detects a plurality of wavelengths.

While the disclosed invention is primarily methodology, a demonstrative Spectroscopic Ellipsometer System as utilized to obtain data, is shown in FIG. 1. Note the presence of a Source of Electromagnetic Radiation (LS), a Polarizer (P) for producing a Polarized beam of electromagnetic radiation (PPCLB), a Rotatable or Rotating Compensator (C), Stage (STG) for supporting a Material System (MS), an Analyzer (A), a Dispersive Optics (DO) and a Detector (DET) comprised of a plurality of Detector Elements (DE), each of which is positioned to intercept a different wavelength. Also indicated is Compensator (C') to show that said Rotatable or Rotating Compensator can be placed on either side of the Material System (MS), or on both sides. Further shown is an optional Focusing Lens (FE) which can be present to converge an electromagnetic beam (EPCLB) which passes through the Analyzer (A), onto the Dispersive Optics (DO). In use, the Polarizer (P) and Analyzer (A) are typically set to an azimuthal angle and held motionless, and the Compensator (C) or (C') is caused to rotate stepwise or continuously while an electromagnetic beam (PPCLB) is caused to impinge upon the Material System (MS) such that spectroscopic data is collected by the Detector (DET).

Figure 2:
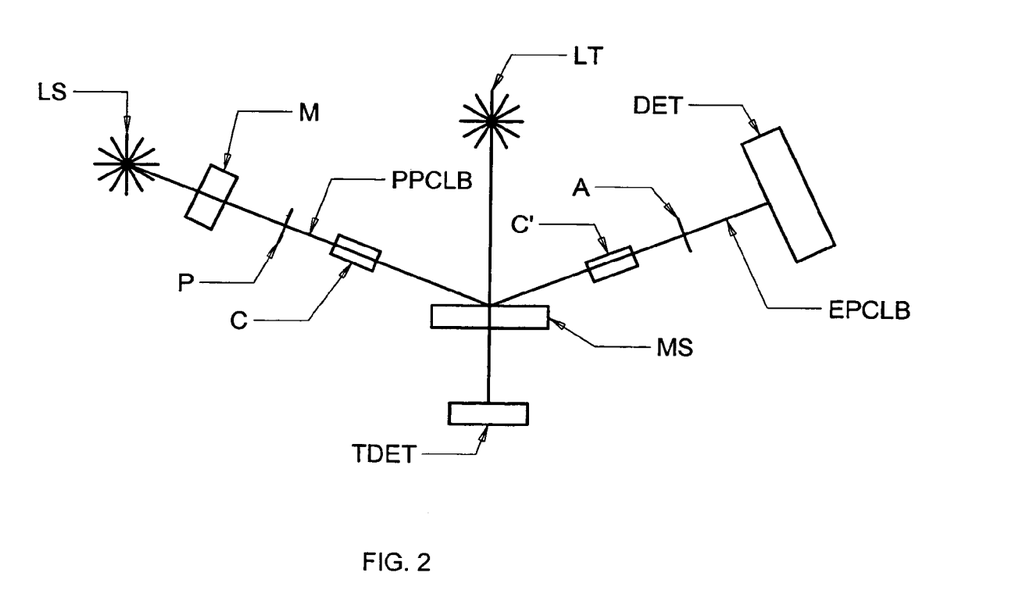
FIG. 2 shows a demonstrative ellipsometer system which includes a monochromator and detects a single wavelength at a time.

FIG. 2 demonstrates an ellipsometer which comprises a Source of Electromagnetic Radiation (LS), a Monochromator (M), a Polarizer (P) for producing a Polarized beam of electromagnetic radiation (PPCLB), optionally a Rotatable or Rotating Compensator (C), Stage (STG) for supporting a Material System (MS), optionally a Rotatable or Rotating Compensator (C'), an Analyzer (A), a Dispersive Optics (DO) and a Detector (DET). Also shown are a Transmission Source (LT) of electromagnetic radiation and a Transmission Detector (TDET), (which it is to be appreciated can also be present in FIG. 1). While the Transmission Source (LT) of electromagnetic radiation and Transmission Detector (TDET) are shown configured to enable use of a beam of electomagnetic radiation which is normally incident to the Sample (MS) Surface, it is to be understood that the Source (LT) can be positioned to effect a non-normal angle of incidence. In use the Source (LS) provides a Spectroscopic Beam of electromagnetic radiation and the Monochromator (M) selects a sequence of single wavelengths which are subjected to polarization by Polarizer (P). An optional Compensator (C), when present, can be applied to modify the polarization state before the single wavelength is caused to interact with and reflect from the Sample (MS) at an oblique angle, then, if it is present, pass through an optional Compensator (C'), said Analyzer (A) and enter the Detector (DET) which monitors each wavelength as it is presented thereto. The method can further comprise causing the Transmission (LT) Source of electromagnetic radiation to direct a beam through said Sample (MS) and into the Transmission Detector (TDET). Said Transmission system can have a Polarizer and Analyzer, and optionally Compensator present, to enable obtaining Transmission Ellipsometric data.

Figure 3A:
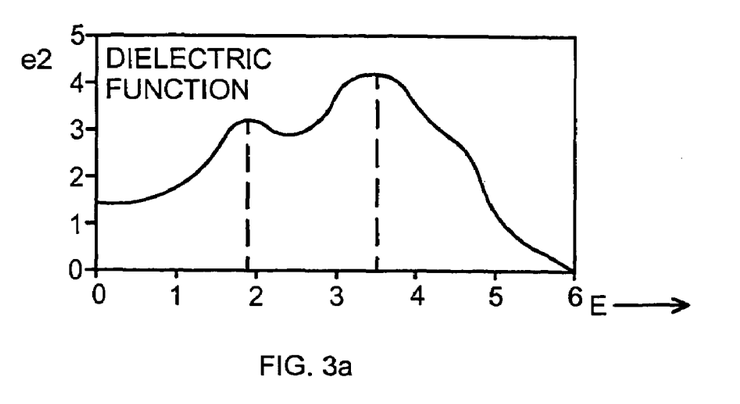
FIGS. 3a, 3b and 3c show a Dielectric Function, a Parameterizing Oscillator Structure, and application of two Parameterizing Oscillator Structures to model a portion of the Dielectric Function, respectively.
Figure 3B:
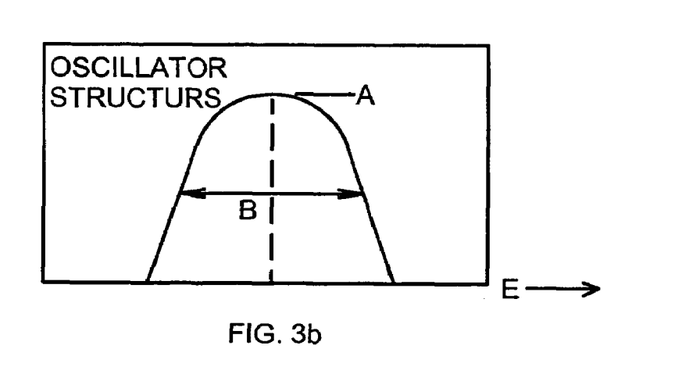
Figure 3C:
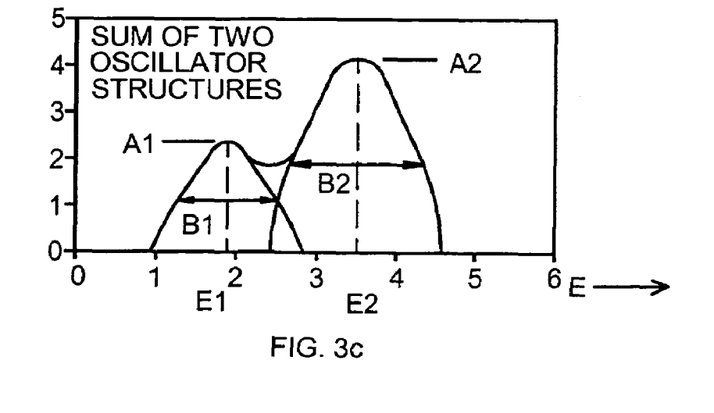

FIGS. 3a, 3b and 3c show an imaginary part of a Dielectric Function, a Parameterizing Oscillator Structure, and application of two Parameterizing Oscillator Structures to model a portion of the Imaginary Part of a Dielectric Function, respectively. A similar plot exists for the Real Part.

It is specifically noted that FIG. 3c requires only A1, A2, B1 and B2 to describe the data of FIG. 3a. It is parameterization of this nature which enables the methodology of the present invention when, for instance, Three (3) layers are present. This is because said Three (3) layers each require, at a minimum, real, and for absorbing material imaginary, parts of the Dielectric Function, and Thickness, to be determined. That means up to Nine (9) parameters require evaluation at each wavelength. However, the data acquired provides PSI and DELTA from the Front and Back of the sample, and a Transmission Intensity Value, (and/or Transmission PSI and DELTA). That means that only Five (5) or Six (6) Data Values are available, as opposed to Nine (9) unknowns for each of a multiplicity of wavelengths. (It is noted that where both Transmission Intensity and Transmission Ellipsometry data are obtained a total of Seven (7) data sets can be achieved). Said Five (5) or Six (6) or Seven (7) Data Values are insufficient to allow direct one for one determination of the up to Nine (9) unknowns at each wavelength. However, where the Four Parameter values A1, A2, B1 and B2 apply over a plurality of wavelengths, the Data corresponding to said Five (5) or Six (6) or Seven (7) Data Points from each of said plurality of wavelenghts becomes sufficient to enable direct one for one determination of the Nine (9) unknowns, and can even enable evaluation of more than said Nine (9) unknowns. (Note, As described in Patent to Herzinger U.S. Pat. No. 5,796,983, which is incorporated by reference herein, describes other Parameter Models applicable in practice of the present invention, which comprise different, or additional defining Parameters). It is further disclosed that where Dielectric Function data is available over a range of wavelengths, but there being only a few Parameters in a parameterized model necessary to evaluate model said data, the data set is actually sufficient in many cases to enable determination of other parameters, such as selections from the group consisting of interface mixing, surface roughness, thickness nonuniformity, grading within layers, birefringence and the like.

Figure 4A:
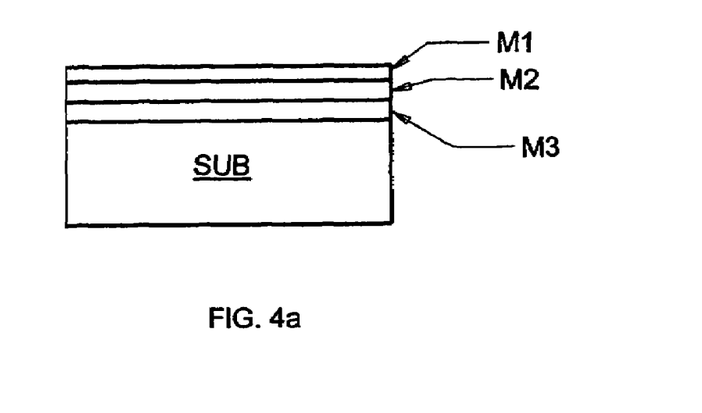
FIGS. 4a and 4b show two embodiments of a sample such as can be investigated by the methodology of the present invention.
Figure 4B:
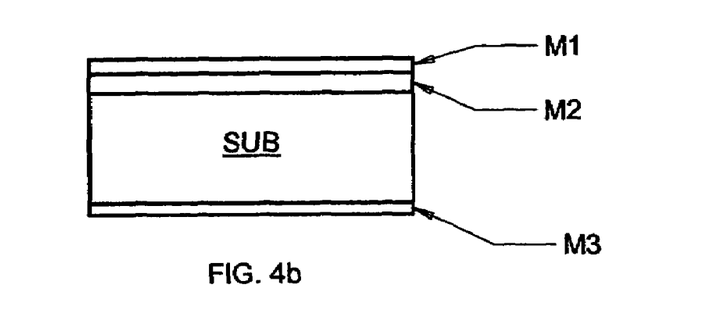

FIGS. 4a and 4b show two embodiments of a sample such as can be investigated by the methodology of the present invention. The layers of material (M1), (M2), (M3) etc. present can all be present on one side of a Substrate (SUB), as shown in FIG. 4a, or can be distributed to both sides, as exemplified in FIG. 4b. It is emphasized that the shown systems are demonstrative and not limiting, and that any functional type of ellipsometer, such as Rotating Analyzer, Rotating Polarizer, Rotating Compensator, etc., (or discrete rotatable versions thereof), and Polarization Modulation, Null etc. can be utilized in practice of the present invention methodology.

It is to be understood that the terminology "step-size" refers to the number of wavelengths between wavelengths at which data is acquired over a range of wavelengths. It is specifically noted that the present invention methodology is characterized in that the obtained data is insufficient to directly one for one evaluate all parameters of the mathematical model over the wavelength range.

Figure 5:
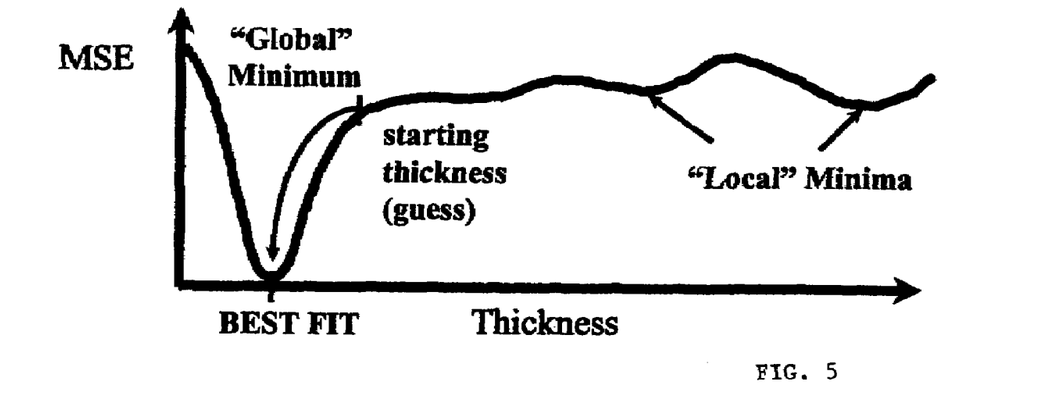
FIG. 5 demonstrates a Mean Square Error (MSE) plot which identifies the benefit provided by use of a Global Fit routine for determining starting values applied in a regression procedure.

Finally, FIG. 5 demonstrates a Mean Square Error (MSE) plot. Note the presence of a Major Minimum and a number of Local Minima. As mentioned earlier, an approach to obtaining good initial "educated guess" values for characterizing parameters in a mathematical model of a sample comprising a plurality of layers, is a technique termed "Global Fitting". The "Global Fit" approach provides that a multiplicity of reasonable combinations of parameters that are to be fit to empirical data by a regression procedure be tested, and the combination which provides the lowest Square Error value be identifed. That combination of values is then entered to the regression procedure which serves to provide best fit values. The Global Fit procedure helps insure that the regression procedure does not return parameter values that correspond to a false Local Square Error minima, but rather correspond to the Best Fit Minima. In more detail, the Global Fit procedure utilized by the J. A. Woollam Co. works by calculating the Mean Square Error (MSE) for parameter combinations which are scanned at intervals over some set range grid. If a lower MSE is found, it is saved in memory until a new lower one is found. Global Fits are usually, though not necessarily, performed on three or fewer parameters because the more parameters which are involved, the greater will be the iteration time. Parameters such as thickness, optical constants, alloy fraction, interface mixing, surface roughness, thickness nonuniformity, grading within layers, birefringence, and incoherent back-surface reflections.

It is to be understood that the terminology "optical constants", dielectric function, "n" and "k", "e1" and "e2" are mathematically equivalent and use of one thereof implies inclusion coverage of the others.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of evaluating a sample comprised of stacked layers of at least:

material 1 and material 2;

present on at least one surface of a substrate having first and second substantially parallel sides;

said method sequentially comprising the steps of:

a) using published data, and/or separate samples of material from each layer and/or educated guessing determining starting values for n and k for said materials 1 and 2 seperately over a range of wavelengths, wherein n is the index of refraction and k is the extinction coefficient, and therefrom determining initial values for parameters in a parameterized mathematical model therefore;

practicing steps b and c in either order or simultaneously:

b) obtaining reflective spectroscopic ellipsometric data from both first and second sides of said sample, and transmission data from at least one side thereof to provide two PSI, two DELTA and transmision intensity data sets;

c) providing a mathematical model of said sample comprising n and k and thickness for each of the material layers, said n and k being parameterized over a plurality of wavelengths as determined in step a;

d) utilizing starting values determined in step a regressing said mathematical model identified in step c, simulaneously onto the five data sets identified in step b;

to evaluate said n, k and thickness defining parameters for the material 1 and material 2 layers in the wavelength range over which said n and k values are parameterized;

said method being characterized in that the obtained data is insufficient to directly one for one evaluate all parameters of the mathematical model over the wavelength range; and e) displaying at least one selection from the group consisting of:
n;
k;
real part of dielectic function;
imaginary part of dielectic function;
thickness;
PSI; and
DELTA;
for at least one selection from the group consisting of:
material 1; and
material 2;
over at least part of the wavelength range over which said n and k values are parameterized.

2. A method as in claim 1, in which the mathematical model further comprises at least one parameter which characterizes at least one selection from the group consisting of:
interface mixing;
alloy fraction;
surface roughness;
thickness nonuniformity;
grading within layers;
birefringence; and
incoherent back-surface reflections.

3. A method as in claim 2, in which an additional step involves determining at least additional step selected from the group:
determining a wavelength range in which said ellipsometric data is sensitive to a selected parameter and using only ellipsometric data at said wavelengths in the regression procedure, with ellipsometric data at wavelengths not sensitive to said selected parameter not being used in said regression procedure, and
using a wavelength range and/or step size in ellipsometric data obtained from the first side of said sample which is not the same as the wavelength range used in ellipsometric data obtained from the second side of said sample.

4. A method as in claim 1, in which material 1 is present on one side of said substrate and material 2 is present on the other side of said substrate.

5. A method as in claim 1, in which steps a and b are merged and in which initial values for n, k and thickness for material 1 and material 2, which initial values are entered to the step d regression procedure, are determined by an educated guess provided by application of a global fit procedure which comprises scanning parameter values through a grid range thereof to determine a combination thereof which provides a lowest square error between empirical data obtained in step b and values calculated by use of the mathematical model.

6. A method of evaluating a sample comprised of a stacked sequence of:
material 1, material 2 and material 3;
present on at least one surface of a substrate having first and second substantially parallel sides;
said method sequentially comprising the steps of:
a) using published data and/or separate samples of material from each layer and/or educated guessing, determining starting values for n and k for said material in each layer separately, wherein n is the index of refraction and k is the extinction coefficient, and therefrom determining initial values for parameters in a parameterized mathematical model therefore;
practicing steps b and c in either order or simultaneously:
b) obtaining reflective spectroscopic ellipsometric data from both first and second sides of said sample, and transmission data from least at least one side thereof to provide two PSI, two DELTA and at least one transmision intensity and/or transmission PSI and DELTA ellipsometric data sets;
c) providing a mathematical model of said sample comprising n and k and thickness for each of the material 1, material 2, and material 3 layers, said n and k for at least a majority of said materials being parameterized over a plurality of wavelengths;
d) utilizing starting values determined in step a regressing said mathematical model which comprises said nine parameters identified in step c, simulaneously onto the at least five data sets identified in step b;
to evaluate n, k and thickness defining parameters for each said material 1, material 2, and material 3 layers in the wavelength range over which said n and k values are parameterized;
said method being characterized in that the obtained data is insufficient to directly one for one evaluate all parameters of the mathematical model over the wavelength range; and
e) displaying at least one selection from the group consisting of:
n;
k;
real part of dielectic function;
imaginary part of dielectic function;
thickness;
PSI; and
DELTA;
for at least one selection from the group consisting of:
material 1;
material 2; and
material 3;
over at least part of the wavelength range over which said n and k values are parameterized.

7. A method as in claim 6, in which the mathematical model further comprises at least one parameter which characterizes at least one selection from the group consisting of:
interface mixing;
alloy fraction;
surface roughness;
thickness nonuniformity;
grading within layers;
birefringence; and
incoherent backsurface reflections.

8. A method as in claim 7, in which an additional step involves determining at least additional step selected from the group:
determining a wavelength range in which said ellipsometric data is sensitive to a selected parameter and using only ellipsometric data at said wavelengths in the regression procedure, with ellipsometric data at wavelengths not sensitive to said selected parameter not being used in said regression procedure, and
using a wavelength range and/or step size in ellipsometric data obtained from the first side of said sample which is not the same as the wavelength range used in ellipsometric data obtained from the second side of said sample.

9. A method as in claim 7, in which the data sets acquired are reflective spectroscopic ellipsometric data from both first and second sides of said sample, and transmission intensity data from one side thereof to provide two PSI, two DELTA and transmision intensity.

10. A method as in claim 7, in which at least one selected from the group consisting of:
material 1;
material 2; and
material 3;
is present on said first side of said substrate, and at least one layer of material is present on said second side of said substrate.

11. A method as in claim 6, in which steps a and b are merged and in which initial values for n, k and thickness for material 1, material 2 and material 3, which initial values are entered to the step d regression procedure, are determined by an educated guess provided by application of a global fit procedure which comprises scanning parameter values through a grid range thereof to determine a combination thereof which provides the lowest square error between empirical data obtained in step b and values calculated by use of the mathematical model.

12. A method of quantifying defining parameters for a plurality of layers of different materials present on a substrate in a sample, comprising obtaining reflection ellipsometric data from both first and second sides of a sample comprising a plurality of layers of different materials and providing a mathematical model of said sample, then regressing said mathematical model onto data obtained from said first and second sides of said sample by a selection from the group consisting of:
utilizing the data sets obtained from first and second sides of the sample simultaneously;
utilizing the data sets obtained from said first and second sides of the sample independently; and
utilizing the data sets obtained from first and second sides of the sample both independently and simultaneously;
to evaluate said sample layer defining parameters;
said method being characterized in that the obtained data is insufficient to directly one for one evaluate all parameters of the mathematical model over the wavelength range; and
displaying at least one quantified defining parameter for at least one of said plurality of layers of different materials on said substrate over said wavelength range.

13. A method as in claim 12, which further comprises obtaining transmission ellipsometry and/or intensity data from at least one of said first and second sides of said sample, and including it in the regression evaluation of said sample layer defining parameters.

14. A method of quantifying defining parameters for a plurality of layers of different materials in a sample comprised of a substrate with first and second substantially parallel sides, said method comprising, in any functional order, the steps of:
a. providing a sample comprised of a substrate having first and second substantially parallel sides that are separated by a thickness, said substrate having a plurality of layers of different materials present on a selection from the group consisting of:
said layers all being present on one side thereof; and
at least one layer being present on each side thereof;
b. determining ranges of wavelengths over which the various layers of materials are sensitive;
c. utilizing wavelengths in ranges determined in step b, to obtain oblique angle reflection ellipsometry spectroscopic data sets from both sides of said sample;
d. providing a mathematical model for said plurality of layers of materials in said sample, said mathematical model comprising n and k and thickness for each layer, said n and k for at least two materials being parameterized over a plurality of wavelengths, wherein n is the index of refraction and k is the extinction coefficient;
then regressing said mathematical model onto data obtained from both sides of said sample by a selection from the group consisting of:
utilizing the data sets obtained from first and second sides of the sample simultaneously;
utilizing the data sets obtained from first and second sides of the sample independently; and
utilizing the data sets obtained from first and second sides of the sample both independently and simultaneously;
to evaluate said sample layer defining parameters in the wavelength range over which said n and k values are parameterized;
said method being characterized in that the obtained data is insufficient to directly one for one evaluate all parameters of the mathematical model over the wavelength range; and
e) displaying at least one selection from the group consisting of:
n;
k;
real part of dielectic function; and
imaginary part of dielectic function; and
for at least one of said plurality of layers;
over at least part of the wavelength range over which said n and k values are parameterized.

15. A method as in claim 14, which further comprises obtaining transmission ellipsometric and/or intensity data from at least one of said first and second sides of said sample, and including it in the regression evaluation of said sample layer defining parameters.

16. A method as in claim 15, in which the mathematical model comprises at least one parameter which characterizes at least one selection from the group consisting of:
interface mixing;
surface roughness;
alloy fraction;
thickness nonuniformity;
grading within layers;
birefringence; and
incoherent back-surface reflections.

17. A method as in claim 14, in which the mathematical model comprises at least one parameter which characterizes at least one selection from the group consisting of:
interface mixing;
surface roughness;
alloy fraction;
thickness nonuniformity;
grading within layers;
birefringence; and
incoherent back-surface reflections.

18. A method as in claim 14, in which at least one of said plurality of layers of materials is present on said first side of said substrate, and at least one material is present on said second side of said substrate.

19. A method as in claim 14, in which initial values for n, k and thickness for the plurality of materials which are entered to the step d regression procedure, are determined by an educated guess provided by application of a global fit procedure which comprises scanning parameter values through a grid range thereof to determine a combination thereof which provides the lowest square error between empirical data obtained in step b and values calculated by use of the mathematical model.

20. A method of quantifying defining parameters for a plurality of layers of different materials on a sample comprising a substrate having first and second substantially parallel sides, said method comprising;

practicing steps a and b in either order or simultaneously:

a) obtaining reflection ellipsometric data from both first and second sides of said sample;

b) providing a mathematical model of said sample, said mathematical model comprising n and k and thickness for each layer, wherein n is the index of refraction and k is the extinction coefficient; said n and k for each material of material being parameterized over a plurality of wavelengths;

c) regressing said mathematical model onto said data obtained from both of said first and second of the sample simultaneously;

to evaluate said sample layer defining parameters in said mathematical model in the wavelength range over which said n and k values are parameterized;

said method being characterized in that the obtained data is insufficient to directly one for one evaluate all parameters of the mathematical model over the wavelength range; and d) displaying at least one selection from the group consisting of:

n;

k;

real part of dielectic function; and imaginary part of dielectic function; and for at least one of said plurality of layers;

over at least part of the wavelength range over which said n and k values are parameterized.

21. A method as in claim 20, in which the step a determination of starting values for n and k for each layer separately is obtained from published data, and/or by obtaining spectroscopic ellipsometric data from separate samples of material for each layer and/or educated guessing, and utilizing said initial values in determination of n and k for said materials.

22. A method as in claim 20, which further comprises obtaining transmission intensity and/or ellipsometric data from at least one of said first and second sides of said sample, and including it in the regression evaluation of said sample layer defining parameters in step c.

23. A method as in claim 20, in which the mathematical model comprises at least one parameter which characterizes at least one selection from the group consisting of:

interface mixing;

surface roughness;

alloy fraction;

thickness nonuniformity;

grading within layers;

birefringence; and incoherent back-surface reflections.

24. A method as in claim 20, in which at least one of said plurality of layers of materials is present on said first side of said substrate, and at least one layer of material is present on said second side of said substrate.

25. A method as in claim 20, in which initial values for n, k and thickness for the plurality of materials which are entered to the step d regression procedure, are determined by an educated guess provided by application of a global fit procedure which comprises scanning parameter values through a grid range thereof to determine a combination thereof which provides the lowest square error between empirical data obtained in step b and values calculated by use of the mathematical model.

26. A method of evaluating a sample comprised of stacked layers of at least:

material 1 and material 2;

present on at least one surface of a substrate having first and second substantially parallel sides;

said method sequentially comprising the steps of:

practicing steps a and b in either order or simultaneously:

a) obtaining reflective spectroscopic ellipsometric data from both first and second sides of said sample, and transmission data from at least one side thereof to provide two PSI, two DELTA and transmision intensity and/or transmission ellipsometric PSI and DELTA data sets;

b) providing a mathematical model of said sample comprising n and k and thickness for each of the material layers, wherein n is the index of refraction and k is the extinction coefficient, said n and k being parameterized over a plurality of wavelengths;

c) determining starting values for n and k and thickness for said material 1 and material 2 parameters in a parameterized mathematical model, by application of a global fit procedure which comprises scanning parameter values through a grid range thereof to determine a combination of values which provides the lowest square error between empirical data and values calculated by use of the mathematical model;

d) utilizing starting values determined in step c regressing said mathematical model identified in step c, simulaneously onto the five or six data or seven sets identified in step a;

to evaluate said n, k and thickness defining parameters for the material 1 and material 2 layers in the wavelength range over which said n and k values are parameterized;

said method being characterized in that the obtained data is insufficient to directly one for one evaluate all parameters of the mathematical model over the wavelength range; and e) displaying at least one selection from the group consisting of:

n;

k;

real part of dielectic function;

imaginary part of dielectic function;

thickness;

PSI; and

DELTA for at least one of said plurality of layers;

over at least part of the wavelength range over which said n and k values are parameterized.

27. A method as in claim 26, in which the mathematical model further comprises at least one parameter which characterizes at least one selection from the group consisting of:

interface mixing;

surface roughness;

alloy fraction;

thickness nonuniformity;

grading within layers;

birefringence; and incoherent back-surface reflections.

28. A method as in claim 27, in which an additional step involves determining at least additional step selected from the group:

determining a wavelength range in which said ellipsometric data is sensitive to a selected parameter and using only ellipsometric data at said wavelengths in the regression procedure, with ellipsometric data at wavelengths not sensitive to said selected parameter not being used in said regression procedure, and using a wavelength range and/or step size in ellipsometric data obtained from the first side of said sample which is not the same as the wavelength range used in ellipsometric data obtained from the second side of said sample.

* * * * *